United States Patent [19]
Wurster et al.

[11] Patent Number: 5,144,953
[45] Date of Patent: * Sep. 8, 1992

[54] LITHOTRIPTOR WITH X-RAY ALIGNMENT SYSTEM

[75] Inventors: Helmut Wurster, Oberderdingen; Werner Krauss, Knittlingen, both of Fed. Rep. of Germany

[73] Assignee: Richard Wolf GmbH, Knittlingen, Fed. Rep. of Germany

[ * ] Notice: The portion of the term of this patent subsequent to Oct. 29, 2008 has been disclaimed.

[21] Appl. No.: 408,835

[22] Filed: Sep. 18, 1989

[30] Foreign Application Priority Data

Nov. 28, 1988 [DE] Fed. Rep. of Germany ..... 38400774

[51] Int. Cl.$^5$ ............................................. A61B 17/22
[52] U.S. Cl. ........................... 128/660.30; 128/24 EL; 378/62; 378/145
[58] Field of Search ........ 128/24 AA, 24 EL, 660.03; 606/127, 128; 378/62, 99, 162, 163, 195, 196, 197, 205

[56] References Cited

U.S. PATENT DOCUMENTS

| | | | |
|---|---|---|---|
| 3,803,417 | 4/1974 | Kok | 378/196 |
| 3,891,845 | 6/1975 | English | 378/58 |
| 3,993,906 | 11/1976 | English | 378/58 |
| 4,705,026 | 11/1987 | Chaussy et al. | 128/24 A |
| 4,771,787 | 9/1988 | Wurster et al. | 128/660.03 |
| 4,819,257 | 4/1989 | Grasser et al. | |
| 4,821,730 | 4/1989 | Wurster et al. | 128/660.03 |
| 4,877,017 | 10/1989 | Hahn et al. | 128/24 A |
| 4,928,672 | 5/1990 | Grasser et al. | 128/24 EL |
| 4,984,565 | 1/1991 | Rattner et al. | 128/24 EL |
| 5,060,634 | 10/1991 | Belikan et al. | 128/24 EL |

FOREIGN PATENT DOCUMENTS

| | | |
|---|---|---|
| 0264738 | 4/1988 | European Pat. Off. |
| 2913251 | 10/1980 | Fed. Rep. of Germany |
| 3426398 | 7/1984 | Fed. Rep. of Germany |
| 8528785 | 10/1985 | Fed. Rep. of Germany |
| 8534425 | 12/1985 | Fed. Rep. of Germany |
| 8515656 | 11/1986 | Fed. Rep. of Germany |
| 3544628 | 6/1987 | Fed. Rep. of Germany |
| 3544707 | 6/1987 | Fed. Rep. of Germany |
| 1333322 | 8/1987 | U.S.S.R. ........................ 128/24 EL |

OTHER PUBLICATIONS

Brochure from Dornier Nierenlithotripter, Jul. 1982.
Philips brochure on the Dornier MFL 5000 Lithotriptor (1987).

Primary Examiner—Ruth S. Smith
Assistant Examiner—Kevin Pontius
Attorney, Agent, or Firm—Panitch Schwarze Jacobs & Nadel

[57] ABSTRACT

The focus of a lithotriptor comprising a transducer for generating focused ultrasonic shock waves is adapted for alignment on a concretion or tissue to be destroyed. The transducer is connected to an image-forming diagnostic X-ray system for locating the concretion or tissue, and comprising an X-ray emitter and an image intensifier disposed on a pivotable frame. The transducer is connected to the X-ray emitter, and the X-ray emitter is disposed at the center of the transducer, so that the emission axes of the transducer and the X-ray emitter coincide.

7 Claims, 8 Drawing Sheets

LITHOTRIPTOR WITH X-RAY ALIGNMENT SYSTEM

FIELD OF THE INVENTION

The invention relates to a lithotriptor comprising a transducer for generating focused ultrasonic shock waves, the focus being adapted for alignment on an object in a patient's body, that is to say a concretion or tissue to be destroyed, and further comprising an image-forming diagnostic X-ray system for locating said object, the X-ray system comprising an X-ray emitter and an image intensifier spaced therefrom and disposed on a frame which is pivotable about an axis in various image planes for the purpose of locating said object.

BACKGROUND OF THE INVENTION

Such a lithotriptor is disclosed for example in the brochure "MFL 5000" by Messrs. C. H. F. Moller (Phillips). In that lithotriptor, an X-ray system locates a concretion as is required before it can be destroyed by ultrasonic shock waves. After the concretion has been successfully located, its three dimensional coordinates are electronically determined. A complicated electronic and mechanical system is then used to guide the transducer until its focus lies in the region defined by the three-dimensional coordinates that have been determined. The ultrasonic shock waves can only then be applied to the concretion to medical advantage.

SUMMARY OF THE INVENTION

A disadvantage of such lithotriptors is that after the concretion to be destroyed has been located, an X-ray system has first to focus the ultrasonic transducer on the concretion so that the patient does not have to be moved from the position at which the concretion was located.

In order to avoid this disadvantage, the X-ray emitter is, according to the present invention, connected to the transducer and is disposed centrally thereof, with the emission axes of the transducer and the X-ray emitter coinciding.

The provision of a complicated electronic and mechanical control system for readjusting or aligning the ultrasonic transducer along the emission axis of the X-ray system, is thereby avoided.

Advantageously, the isocentre of the pivotal motion of the X-ray system, or the frame thereof, is the said focus, and an imaginary extension of the pivotal axis of the frame intersects the focus in each pivotal position of the X-ray system.

This feature avoids the need to align the unit comprising the X-ray emitter and the ultrasonic transducer along its axis, since the ultrasonic transducer is always focused on the concretion or tissue, to be destroyed, when the X-ray system is pivoted in order to locate it.

If the shock waves generated by the transducer are transmitted to the patient's body via a liquid coupling medium, a gas-inflatable balloon may be disposed in the transducer, which balloon, when inflated, displaces the coupling medium in a given region about the axis of the X-ray emitter. When therefore the X-ray system is operated in order to locate the concretion or tissue, the balloon is filled with gas, so that the liquid coupling medium is displaced in a large enough region, thereby to ensure that the X-rays are not appreciably attenuated in transit to the patient's body. After the concretion or tissue to be destroyed has been successfully located in the patient's body, the gas is sucked from the balloon, so that the ultrasonic shock waves emitted by the transducer for destroying the concretion or tissue are conveyed to the patient's body by the coupling medium throughout the entire coupling region.

The ultrasonic transducer may be piezoelectronic or magnetostrictive or eddy-current in operation, or a transducer having a spark discharge gap can be used. The transducer may be cup-shaped, so that the ultrasonic waves transmitted thereby are already focused. If a plane ultrasonic transducer is used, a suitable lens, in addition to the transducer, must be provided in the path of the ultrasonic waves, so as to focus them.

At least one ultrasonic locating transducer may be connected to the shockwave transducer. The ultrasonic locating transducer may be, for example, a B-scanner connected to the main transducer so as to be capable of scanning the focal region thereof. This enables the concretion or tissue to be scanned by ultrasonic means as well as by X-rays. The operator can, therefore, use either method at choice, or both together. In the latter case, when the balloon has been inflated with gas so that the X-rays can travel through the patient's body without sensible attenuation by the coupling medium, the balloon must be deformed to ensure that the ultrasonic waves emitted by the ultrasonic locating transducer or transducers can reach the target region and receive waves reflected therefrom without appreciable obstruction by the balloon.

Both methods of location can be used without having to move the patient. In addition, it is unnecessary to replace one system of location by the other. This has the advantage that, for example, a diaphragm adjacent to the patient's body and enclosing the aforementioned coupling medium remains at a constant pressure. It is therefore unnecessary to move the patient's body, with the risk of altering the position, for example, of the concretion to be destroyed.

Advantageously, a drive may be provided for positioning the X-ray system and the shock-wave transducer over, or on, the patient's body. The drive may be movable along the X, Y and Z coordinates for positioning the focus of the shock-wave transducer on the concretion or tissue to be destroyed. Preferably, a treatment table on which the patient lies, is formed with an opening for the passage of the X-rays and the ultrasonic waves, the part of the patient's body containing the concretion or tissue to be destroyed, being positioned over said opening.

Alternatively, the concretion or tissue to be destroyed may be aligned on said focus by moving the treatment table along the X, Y and Z coordinates, the X-ray system and the shock-wave transducer being mounted for pivotal movement about the focus of the shock-wave transducer with said focus being stationary relative to said X, Y and Z coordinate system.

For simple positioning of the X-ray system and the shock-wave transducer, the X-ray system and the transducer may be disposed on the frame, which is movable in the direction of the Y and Z coordinates by a drive engaging a column, and is pivotable through a first angle about the axis of the column and through a second angle about the pivotal axis of the frame.

DETAILED DESCRIPTION OF THE INVENTION

Hereinafter, like parts are identified by like referenced numerals.

Figure 1:
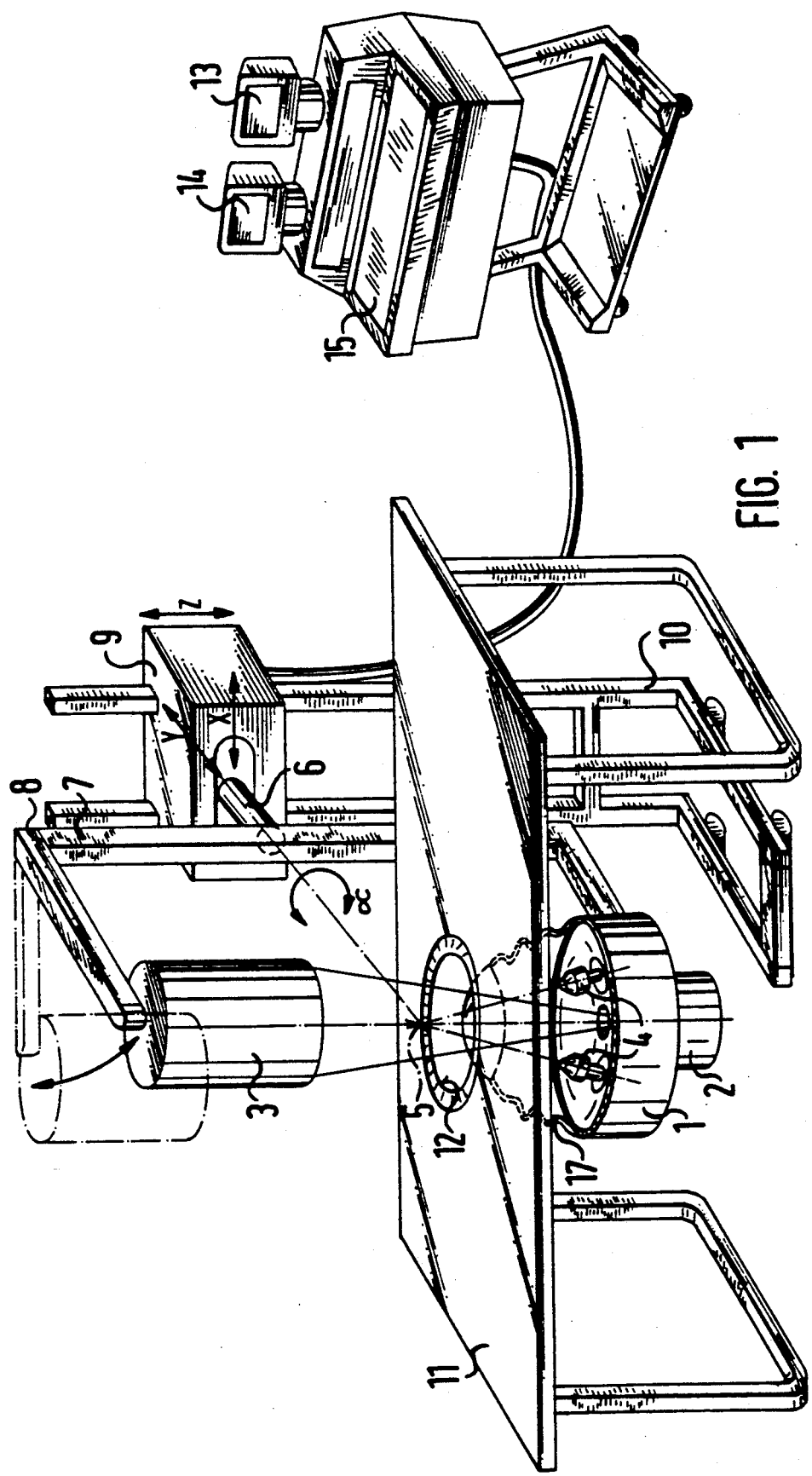
FIG. 1 is an isometric view of a lithotriptor according to a first embodiment of the invention, disposed on a treatment table, in conjunction with a control device.

The lithotriptor includes, as shown in FIG. 1, a unit comprising a cup-shaped ultrasonic transducer 1 and an X-ray emitter 2 connected thereto, which unit is described in detail below, and is disposed on one projecting arm of a U-shaped frame 7. An image intensifier 3 opposite to the unit 1, 2 is secured to the other projecting arm of frame 7. The frame 7 is pivotable on a shaft 6 driven by a drive 9 disposed on a movable stand 10 so that the U-shaped frame 7 can be pivoted through an angle about the shaft 6. The drive 9 can also move the frame 7 in X, Y and Z directions as indicated in FIG. 1.

By means of drive 9, therefore, the frame 7 and thus the X-ray system 2, 3 and the ultrasonic transducer 1 can be exactly positioned above a treatment table 11 between said projecting arms of the frame 7.

The treatment table 11 is formed with an opening 12 over which is placed that part of a patient's body which contains a concretion or tissue to be destroyed.

The X-ray emitter 2 is permanently connected to the transducer 1 and is disposed in the centre thereof so that the emission axes of the transducer 1 and the emitter 2 coincide. According to the present embodiment, two ultrasonic locating transducers 4 in the form of B-scanners are disposed in the cup of the transducer 1, so that the concretion or tissue to be destroyed can be located by ultrasonic means as well as by means of X-rays.

The frame 7 has a pivot point 8 about which the upper arm of the frame 7 carrying the image intensifier 3 is pivotable to one side, so as not to obstruct the operator when the lithotriptor is being used to locate the concretion or tissue by ultrasonic means only.

FIG. 1 also shows the X-ray emitter 2 disposed under the table, so that the operator is subjected only to slight exposure to X-rays.

The lithotriptor is connected to a control device comprising a control panel 15. Monitors 13 and 14 display the images obtained by X-ray or ultrasonic location.

The focus 5 of the ultrasonic transducer 1 is the isocentre for the pivotal motion of the X-ray system 2, 3 or the frame thereof, so that during each pivotal movement of said system, an imaginary extension of the axis of the shaft 6 about which the frame 7 pivots, intersects the focus 5 at an angle.

Figure 2:
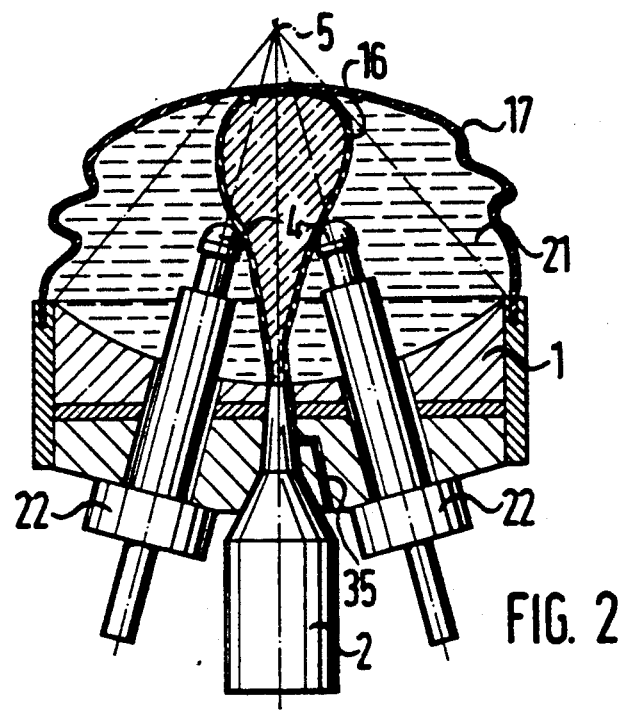
FIG. 2 is an enlarged axial sectional view of a unit of the lithtriptor shown in FIG. 1, comprising an ultrasonic transducer, an X-ray emitter and two B-scanners.

FIG. 2 shows the said unit comprising the ultrasonic transducer 1 and the X-ray emitter 2, and which also comprises the two locating transducers 4.

As shown, the ultrasonic transducer 1 has a central opening through which X-ray emitter 2, connected thereto, can emit radiation.

In order to improve the coupling of the ultrasonic transducer to the patient's body, the cup of the transducer 1 is filled with a liquid coupling medium 21, for example water, and is enclosed by means of a diaphragm 17.

A balloon 16 disposed in the said central opening is inflatable with a gas, the inlet and outlet 35 of the balloon 16 being sealed from the coupling medium 21. When the balloon 16 is inflated, the coupling medium 21 is displaced from a certain region about the axis of the X-ray emitter 2, so that the X-rays reach the patient's body, substantially without attenuation.

Figure 3:
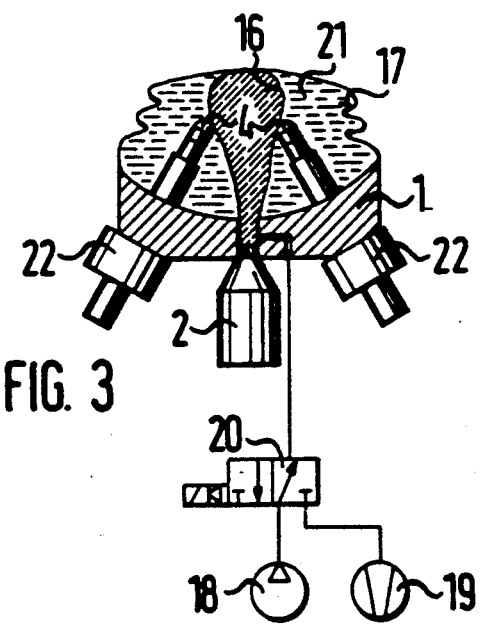
FIG. 3 is a similar view to that of FIG. 2, but drawn to a smaller scale and showing the unit of FIG. 2 connected to a pneumatic system.

The balloon 16 is inflated or deflated by means of a pressure pump 18 and an evacuating pump 19, respectively, (FIG. 3), connected to the balloon 16 by way of a change-over valve 20 and a connecting line.

Each ultrasonic locating transducer 4 is connected to a scanner drive 22 for displacing it along its longitudinal axis.

Figure 4:
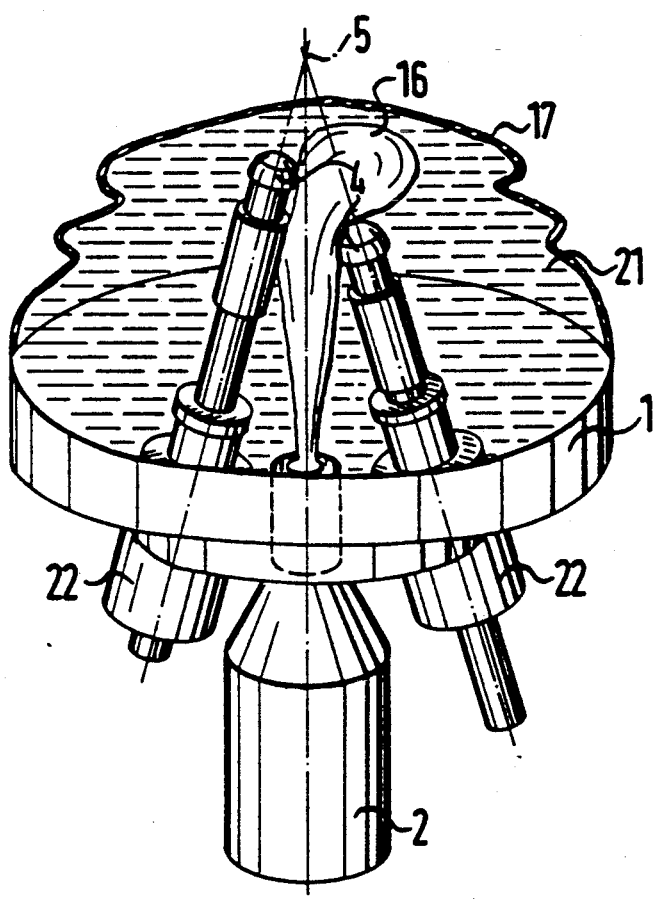
FIG. 4 is an enlarged diagrammatic view showing the unit in FIG. 2 with a gas inflatable balloon therein half-inflated.

FIG. 4 shows the unit 1, 2, 4 with the balloon 16 only half-filled. As will be apparent from that Figure, the left hand locating transducer 4 can be used to locate the concretion or tissue to be destroyed, without completely emptying the balloon 16. To this end, the scanner drive 22 of that transducer 4 moves it axially in the direction of the focus 5, the partially filled balloon 16 being pushed to one side by said left hand transducer 4 so that the ultrasonic waves emitted thereby can enter the patient's body unobstructed by the balloon 16.

Figure 5:
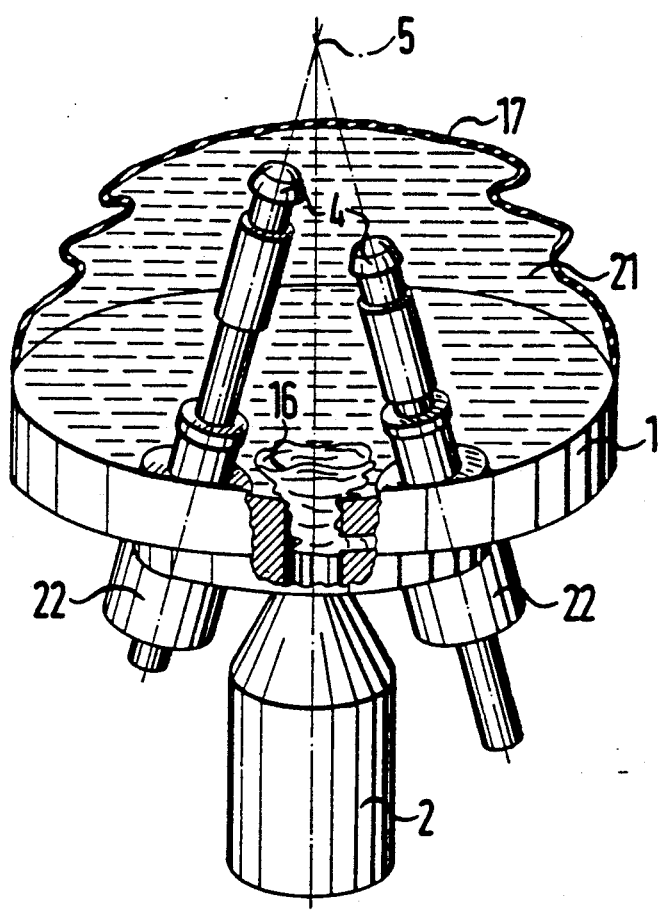
FIG. 5 is a similar view to that of FIG. 4 but showing the balloon in a retracted condition.

FIG. 5 shows the unit 1, 2, 4 when the balloon is completely empty. The balloon must be empty when the ultrasonic shock waves generated by the ultrasonic transducer 1 are applied in order to destroy the concretion or tissue. X-ray location is, of course, impossible in the region of destruction, but a concretion can be located ultrasonically by the transducer 4, even when the ultrasonic shock waves are being applied, so that the process of destruction of the concretion can be observed in real time.

Figure 6:
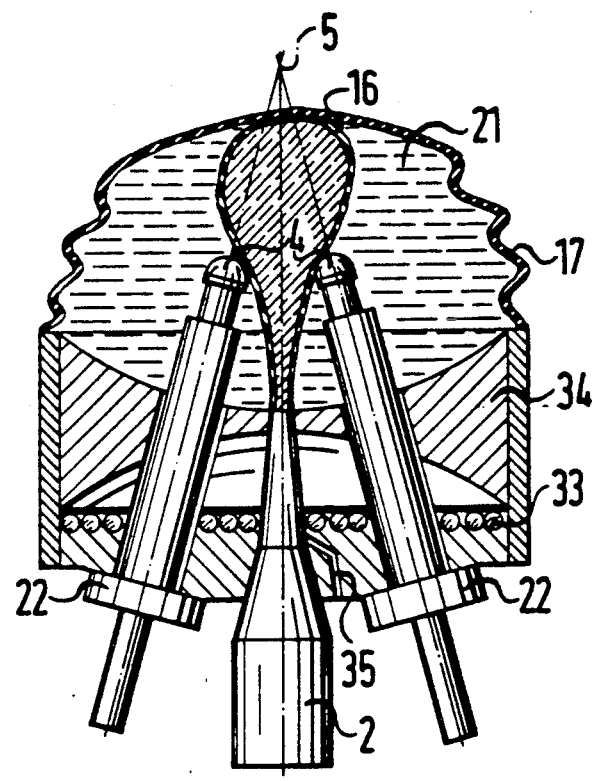
FIG. 6 is a similar view to that of FIG. 2 but showing a modified form of said unit, comprising the X-ray emitter, the ultrasonic transducer and two B-scanners using a planar ultrasonic transducer and a lens.

According to the modification of FIG. 6, the cup-shaped ultrasonic transducer is replaced by a planar ultrasonic transducer 33, the shock waves being concentrated at focus 5 by means of an acoustic lens 34.

Figure 7:
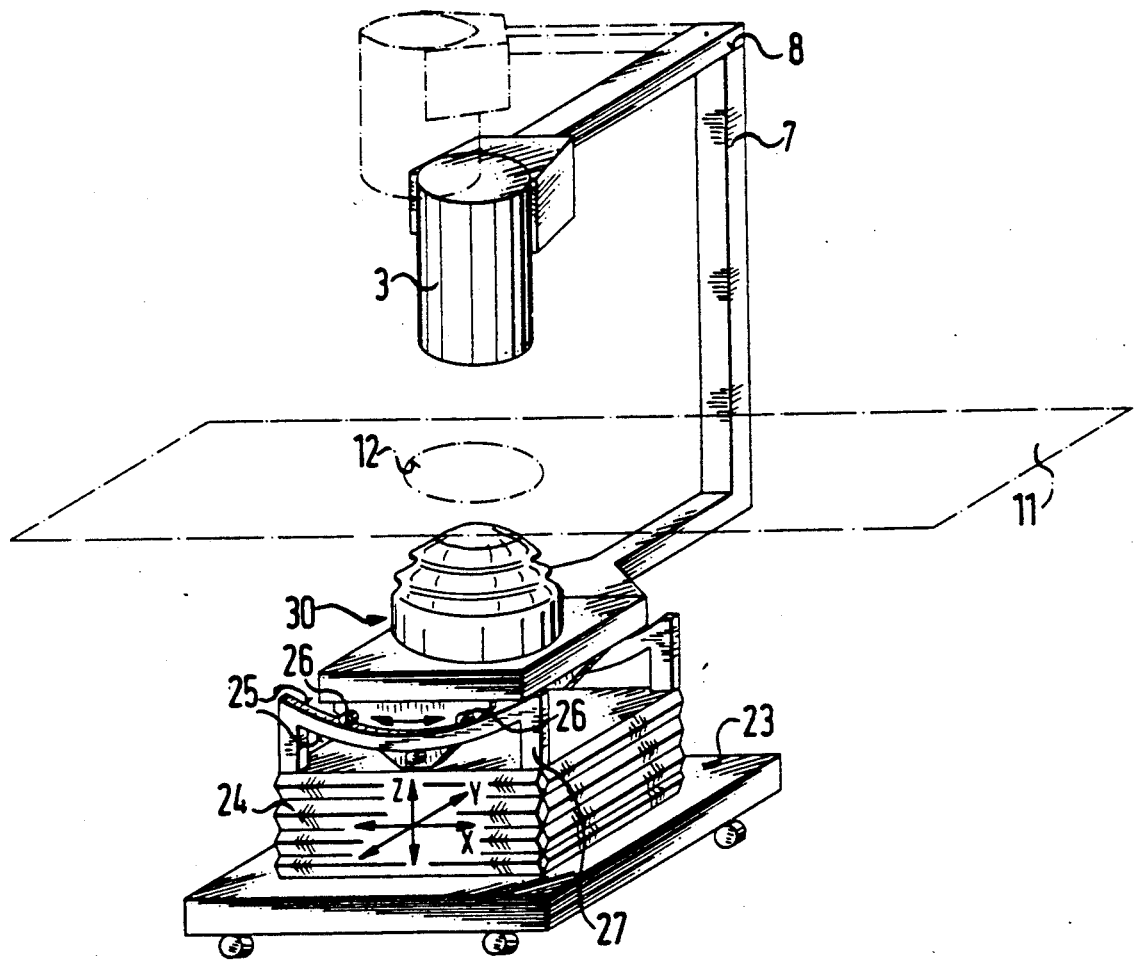
FIG. 7 is an isometric view of a lithotriptor according to a second embodiment of the invention, a treatment table being shown schematically.

In the embodiment of FIG. 7, in contrast to the embodiment of FIG. 1, the focus 5 of the said unit (hereinafter identified by the reference numeral 30) comprising the ultrasonic transducer 1, X-ray emitter 2, etc., is positioned with respect to the concretion or tissue to be destroyed, by means of a drive 24 beneath the table 11 and being secured to a carriage 23, the drive 24 being adapted to move the frame 7 in the X, Y or Z directions.

The frame 7 can also be pivoted in the manner described above for locating the concretion, by means of motor-driven rollers 26 which are permanently connected to frame 7 and roll on arcuate guides 25 on the drive 24.

Figure 8:
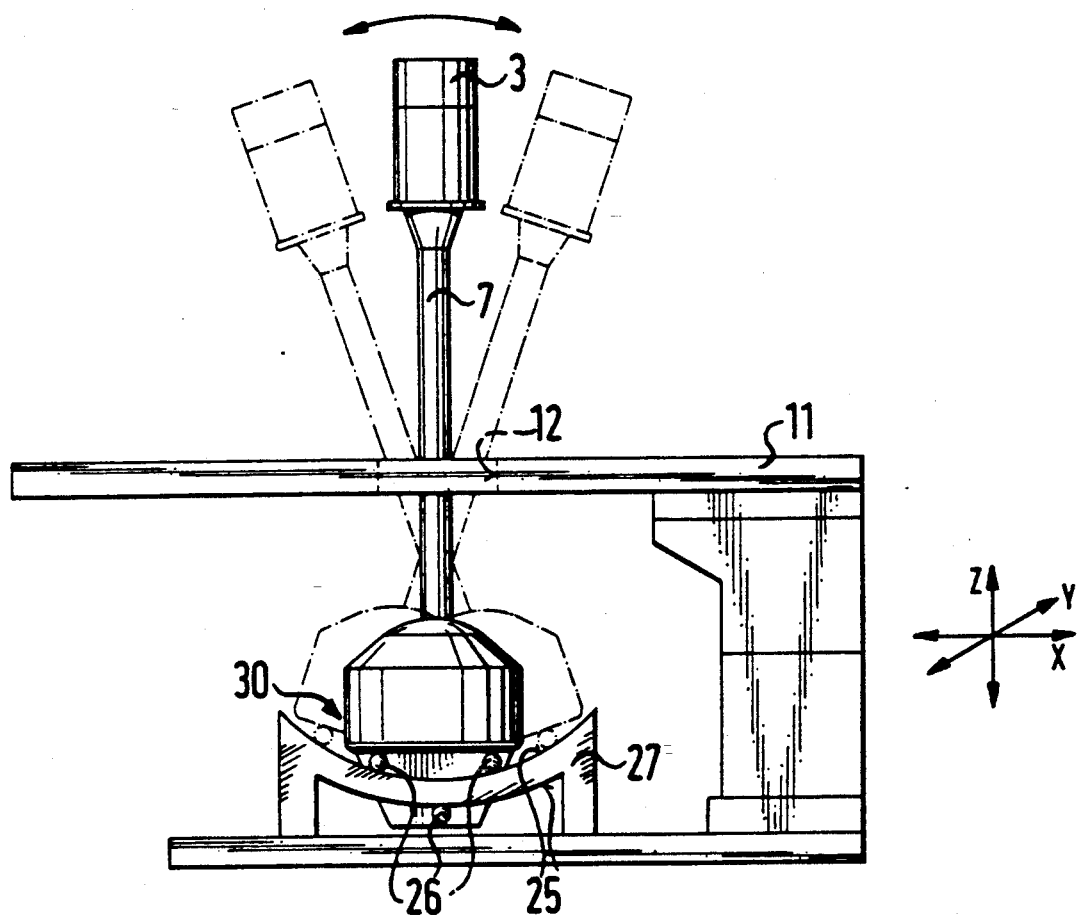
FIG. 8 is an elevational view of a lithotriptor according to a third embodiment of the invention disposed on a treatment table, which is movable in X, Y and Z directions.

According to the embodiment of FIG. 8, a treatment table 11 is movable in translation in the X, Y and Z directions and is adapted to carry a patient for movement in such directions in order to position the concretion or tissue to be destroyed on the focus of unit 30. As in the embodiment of FIG. 7, the pivotal motion for locating the concretion is brought about by means of rollers 26 moving on arcuate guides 25.

Figure 9:
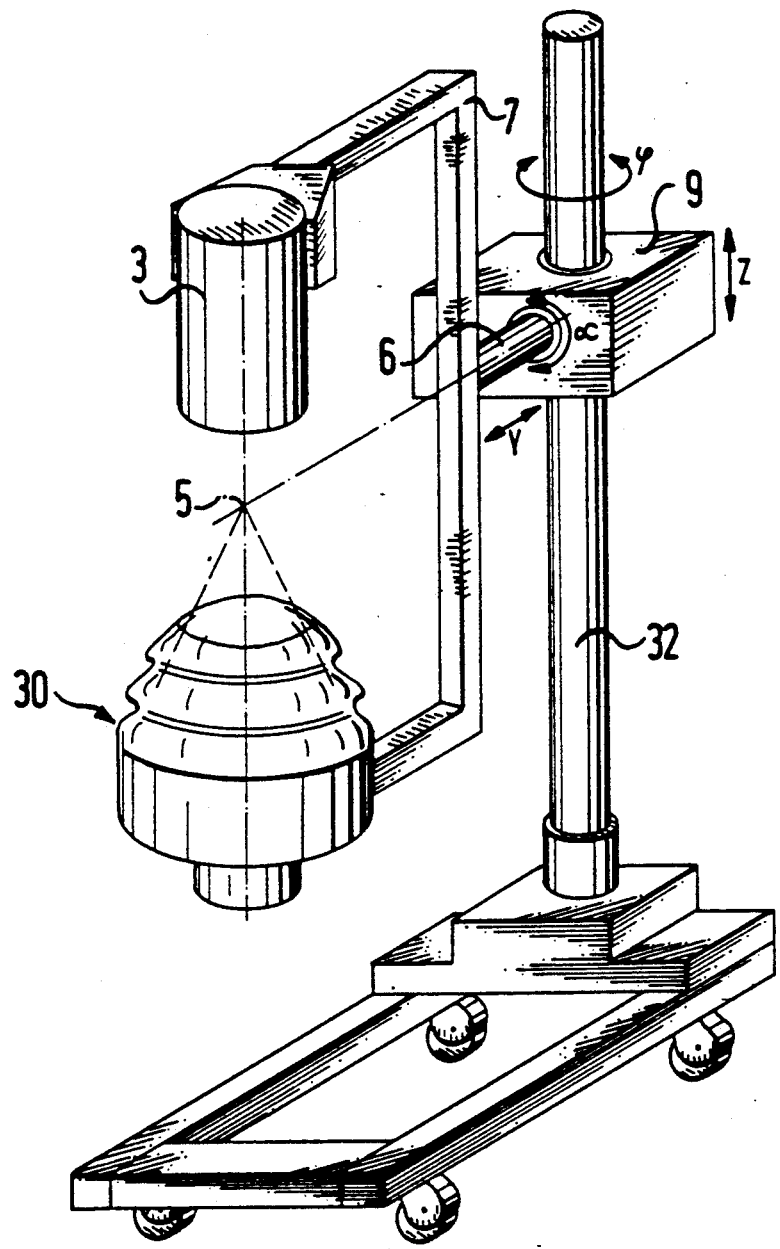
FIG. 9 is an isometric view of a lithotriptor according to a fourth embodiment of the invention.

In the embodiment of FIG. 9, the unit 30 and the image intensifier 3 are mounted on a frame 7 which is movable in the vertical direction on a shaft 6 by a drive 9 engaging a vertical pillar 32. The drive 9 can also be used for moving the shaft 6 in the direction of the Y coordinate and for pivoting it through an angle about the axis of the column 32 and for pivoting the frame 7 through an angle about the pivotal axis of the shaft 6.

What is claimed is:

1. A lithotriptor comprising a transducer for generating focused ultrasonic shock waves for destroying an object in a patient's body; means for aligning the focus of the transducer on said object; a frame for supporting said transducer; an image-forming diagnostic X-ray system for locating said object, said X-ray system comprising an X-ray emitter and an image intensifier spaced therefrom, and disposed on said frame, said frame being pivotable about a pivotal axis in a plurality of image planes, for location of said object, wherein the X-ray emitter is connected to said transducer and disposed centrally thereof with the emission axis of said transducer coinciding with that of the X-ray emitter; means containing a liquid coupling medium for the transmission of ultrasonic shock waves generated by said transducer to the patient's body; and a balloon disposed in said coupling medium and which is inflatable by means of a gas to displace said medium in a region encompassing the entire length of the axis of the X-ray emission which passes through said coupling medium.

2. A lithotriptor as claimed in claim 1 wherein said focus is the isocenter for the pivotal movement of the X-ray system, an imaginary extension of the pivotal axis of the frame intersecting said focus in each pivotal position of said frame.

3. A lithotriptor as claimed in claim 1 wherein at least one ultrasonic transducer for locating said object is connected to said ultrasonic transducer for generating said shock waves.

4. A lithotriptor as claimed in claim 3 further comprising gas evacuation means for at least partially deflating said balloon so that ultrasonic waves emitted by said transducers can enter the patient's body unobstructed by said balloon.

5. A lithotriptor as claimed in claim 3 wherein said locating transducer is displaceable along its longitudinal axis toward said focus.

6. A lithotriptor as claimed in claim 1 wherein said means for aligning comprise means for moving said X-ray system and said transducer along X, Y and Z coordinates, thereby aligning said focus on said object.

7. A lithotriptor as claimed in claim 1 wherein said means for aligning comprise drive means engaging a column and being pivotable thereabout for moving said frame in the direction of X and Z coordinates, and for moving said frame about said pivotal axis thereof, said X-ray system and said transducer being disposed on said frame.

* * * * *